United States Patent
Sun et al.

(10) Patent No.: US 6,906,220 B2
(45) Date of Patent: Jun. 14, 2005

(54) PROCESS TO PRODUCE 4-(2-SULFOETHYL) CYCLOHEXANE, 1,2-DIOL SODIUM SALT FROM 4-VINYLCYCLOHEXANE-1,2-DIOL

(75) Inventors: Yanhui Sun, Wilmington, DE (US); Shaorong Chen, Wilmington, DE (US)

(73) Assignee: Invista North America S.àr.l., Wilmington, DE (US)

( * ) Notice: Subject to any disclaimer, the term of this patent is extended or adjusted under 35 U.S.C. 154(b) by 114 days.

(21) Appl. No.: 10/396,085

(22) Filed: Mar. 24, 2003

(65) Prior Publication Data

US 2004/0192971 A1 Sep. 30, 2004

(51) Int. Cl.[7] ............................................. C07C 309/00
(52) U.S. Cl. ....................... 562/120; 562/109; 562/115; 562/30
(58) Field of Search ................. 562/120, 109, 562/115, 30

(56) References Cited

U.S. PATENT DOCUMENTS 2,793,229 A     5/1957   Blaser et al.
6,312,805 B1 *  11/2001  Sun ........................... 428/364

FOREIGN PATENT DOCUMENTS

JP          61-282354        12/1986

OTHER PUBLICATIONS

CA:127:4966 abs of Toxicological and Environmental Chemistry by Mash 57(1–4) pp 153–162 1996.*
CA:122:239210 abs of Neftekhimiya by Alimardanov et al 34(4) pp 344–50 1994.*
Hans–Fischer–Gesellschaft, 29 Bis 30, Sep. 1960 in Munchen, pp. 69–71 (Angew. Chem 73 Jahrg. 1961).
Synthesis of Highly Water–Soluble Cyclodextrin Sulfonates by Addition of Hydrogen Sulfite to Cyclodextrin Allyl Ethers. Gerhard Wenz and Thomas Hofler. Carbohydrate Research 322 (1999) 153–165.
The Peroxide Effect in the Addition of Reagents to Unsaturated Compounds. IVIII. The Addition and Substitution of Bisulfite. M. S. Kharasch, Ernest M. May, and Frank R. Mayo. J. Org. Chem. v. 3, 1938–39, pp. 175–192.

* cited by examiner

*Primary Examiner*—Samuel Barts

(57) ABSTRACT

Disclosed herein is a process for preparing 4-(2-sulfoethylcyclohexane)-1,2-diol sodium salt, at ambient condition and in the presence of a buffer and an initiator, from vinylcyclohexane-1,2-diol. Also disclosed is a process for preparing 3-(2-sulfoethyl) hexanedioic acid, sodium salt by oxidizing 4-(2-sulfoethylcyclohexane)-1,2 diol sodium salt with hydrogen peroxide in the presence of tungstic acid.

9 Claims, No Drawings

PROCESS TO PRODUCE 4-(2-SULFOETHYL) CYCLOHEXANE, 1,2-DIOL SODIUM SALT FROM 4-VINYLCYCLOHEXANE-1,2-DIOL

FIELD OF THE INVENTION

The invention relates to a process to produce 4-(2-sulfoethyl)cyclohexane-1,2-diol sodium salt (SECD) which is a precursor for a cationic dyeability modifier, 3-(2-sulfoethyl) hexanedioic acid, sodium salt (SEHA), for polyesters and polyamides, from 4-vinylcyclohexane-1,2-diol.

BACKGROUND OF THE INVENTION

Polyesters and polyamides have excellent fiber properties, however, polyesters, especially polyester fibers are difficult to dye. Polyamides are not as difficult to dye as polyesters, but one or more dyeability additives are commonly incorporated into polyamides in order to selectively increase the affinity of the polyamide fibers for certain type of dyes or the resistance of the fibers to staining with certain type of staining agents.

U.S. Pat. No. 6,312,805 B1 discloses a process for the synthesis of SEHA involving a sulfonation reaction of 4-vinylcyclohexane-1,2-diol (VCHD), where the pH of sulfonation reaction is maintained at 6.3–6.5 by adding sodium hydroxide solution occasionally to the reaction system. The pH control method disclosed in U.S. Pat. No. 6,312,805 may be difficult in larger scale since mixing takes considerable time. As a result, the concentration of solution is localized and the pH is not uniform. When the solution pH fluctuates, more impurities can be formed, reducing product yield and creating a difficult purification process.

Furthermore, the use of sodium hydroxide to control the pH results in sodium sulfate in the final product (SEHA) solution. The sodium sulfate has very low solubility and it crystallizes before SEHA does, thus a filtration step to remove sodium sulfate is necessary. Even after the filtration, sodium sulfate residue in SEHA crystals is still difficult to be removed. SEHA crude product may need to be recrystallized repeatedly in order to reduce the sodium sulfate level to ≦0.1%. It would be desirable to have a process for producing SEHA with increased yield and with less generation of impurities so that purification is easier and the cost of production is low. The present invention simplifies the process described in U.S. Pat. No. 6,312,805 by eliminating one filtration step, which also improves purity of SEHA.

JP Kokai 61-282354 describes a sulfonation reaction with hydrogen sulfite salt at pH 6.5–7.0 by using a base, or an inorganic salt, such as sodium hydroxide and sodium sulfite. Such combination allows the reaction to reach high yield.

In many literature reports, about 0.5–1 equivalent of sodium sulfite is combined with 1 equivalent sodium bisulfate. This introduces a significant amount of sodium sulfite into the solution. The product separation can be difficult and costly. Helberger (Angew. Chem., 73, 69, 1961) reported that at pH 4, the sulfonation reaction of allyl alcohol produces virtually all the sulfonate-sulfinate bisubstituted product. To get a mono substituted sulfonate, one has to carry out the reaction at a pH higher than 4. G. Wenz and T. Holfer carried out sulfonation reaction on cyclodextrin allyl ethers (Carbohydrate Research 322, 153–165, 1999) using $KNO_3$ as the initiator and sodium hydroxide to adjust pH to 7.1 M. S. Kharasuch et al (J. Org. Chem., V.3 175, 1938) used ammonia to buffer the sulfonation reaction of sodium bisulfate with vinyl group.

U.S. Pat. No. 2,793,229 discloses a process in which a buffer system to make the sulfonation reaction most efficient. Dilute mineral acids are used, namely sulfuric acid.

It is desirable to have a process to produce SEHA wherein there is an ability to control the reaction to the direction of forming mono-substitution. The present invention provides such a process, by employing a minimum amount of a buffer system.

SUMMARY OF THE INVENTION

Disclosed herein is a process for making 4-(2-sulfoethyl) cyclohexane-1,2-diol sodium salt, (SECD), said process comprising contacting 4-vinylcyclohexane-1,2-diol with a sulfonating agent in the presence of a buffer solution and an initiator, at ambient conditions.

DETAILED DESCRIPTION OF THE INVENTION

The present invention discloses a process for preparing 4-(2-sulfoethyl) cyclohexane-1,2 diol sodium salt, (SECD), which, in time, is used to prepare 3-(2-sulfoethyl) hexanedioic acid, sodium salt (SEHA). The 4-(2-sulfoethyl) cyclohexane-1,2-diol sodium salt, (SECD) is prepared from 4-vinylcyclohexane-1,2-diol (VCHD). VCHD is contained with a sulfonating agent in the presence of a buffer solution and an initiator, at ambient condition.

The sulfonating agent is selected from the group consisting of sodium bisulfite and ammonium bisulfite. Preferred is sodium bisulfite.

The buffer solution is selected from the group consisting of alkali metal and ammonium phosphates, bicarbonates and acetates. Some specific examples of these include, but are not limited to, sodium phosphate, sodium bicarbonate, sodium acetate, potassium phosphate, potassium acetate, ammonium phosphate, ammonium bicarbonate, and ammonium acetate. Preferred is ammonium phosphate, and most preferred is sodium phosphate. The buffer is added into solution at the beginning of the reaction.

When a sodium phosphate buffer is used, it can be converted to sodium phosphate monobasic at low pH during the preparation of SEHA. Sodium phosphate monobasic has a very high solubility in water, therefore, it would not precipitate from the solution. As a result, there is no need to perform a filtration step before SEHA crystals form.

When using sodium hydroxide or sodium bisulfite to adjust pH, a filtration step is necessary to remove sodium sulfate by product before SEHA crystallization. Again due to its high water solubility, phosphate salt stays in solution, its content in SEHA crystals is low, which improves SEHA purity. The use of a low level sodium phosphate buffer in this invention reduces the byproducts in the reaction system.

By adding sodium phosphate to the solution, the pH can be maintained at a relatively stable range. The reaction generates less impurity in the product.

The initiator selected is one that can accomplish the initiation of the sulfonation reaction. The initiator can be selected from the group consisting of hydrogen peroxide, sodium bisulfite, sodium persulfate, and potassium persulfate. Preferred is sodium bisulfite, and most preferred is hydrogen peroxide. Hydrogen peroxide is as efficient as sodium persulfate, however, its by-product is water, which has no negative effect on product purity. A reduced excess of sodium bisulfite than reported in U.S. Pat. No. 6,312,805 and the replacement of sodium persulfate by hydrogen peroxide as initiator help to reduce sodium sulfate by-product level.

One embodiment of the process of the present invention is wherein the 4-vinylcyclohexane-1,2-diol that is used is prepared by contacting 4-vinylcyclohexene-1,2-epoxide with water in the presence of a solid acidic catalyst at ambient conditions for a time sufficient to prepare 4-vinylcyclohexane-1,2-diol, which is exemplified herein. Acidic catalysts that are useful in the present invention include silica alumina, $TiF_4/SiO_2$, Amberlyst-15, Dowex-HGR-W2H, Dowex-M33, Dowex-MSC-1-H, Dowex M-31, and NAFION.

Another embodiment of the process of the present invention is wherein the 4-vinylcyclohexane-1,2-diol is prepared by contacting 4-vinylcyclohexene with formic acid in the presence of hydrogen peroxide to form a mixture A comprising at least one of 4-vinylcyclohexane-1,2-diformate; 4-vinylcyclohexane 1-formate-2-ol; 4-vinylcyclohexane-1-ol-2-formate; and 4-vinylcyclohexane-1,2-diol; contacting mixture A with sodium hydroxide to accomplish hydrolysis of at least a portion of the compounds in mixture A to produce a mixture B, said mixture B comprising an aqueous phase and an organic phase; and separating the aqueous phase from the organic phase in mixture B, and obtaining an organic phase comprising essentially of 4-vinylcyclohexane-1,2-diol.

Another embodiment of the process of the present invention is wherein the 4-(2-sulfoethylcyclohexane)-1,2-diol sodium salt is converted to 3-(2-sulfoethyl) hexanedoic acid, sodium salt by oxidizing with hydrogen peroxide in the presence of tungstic acid.

EXAMPLES

Example 1

Synthesis of 4-vinylcyclohexane-1,2-diol (VCHD) from 4-vinylcyclohexene-1,2-oxide (VCHO)

1-A. Hydrolysis of 4-vinylcyclohexene-1,2-oxide (VCHO) by Perchloric Acid

A 1-liter three-neck round flask equipped with a mechanical stirrer, thermometer, and a dropping funnel was charged with 600 mL tetrahydrofuran (THF). 52 mL. VCHO (0.4 mol) was added into the flask. The solution was cooled down to 0° C. in an ice-bath. 22.96 g. perchloric acid (70%) was dissolved in 80 mL D.I. water, and added into the solution dropwise during a period of one hour. The solution temperature was controlled at below 5° C. After the addition of perchloric acid, the ice-bath was removed, and the solution was stirred for 2 hrs at room temperature. Then, 28-g. potassium carbonate in 40 mL water was added to neutralize perchloric acid. The mixture was roto-vaporated to remove some THF. The residue was extracted with ether. After drying the ether solution with anhydrous potassium sulfate, the ether solvent was removed by rotovap. The crude VCHD was distilled at a reduced pressure. VCHD product was collected at 99–106° C. under 0.05 mm Hg. pressure.

1-B. Hydrolysis of 4-vinylcyclohexene-1,2-oxide (VCHO) in the Presence of Solid Acid Catalyst (Acidic Ionic Resin)

63.86 g. VCHO (0.5 mol) was added in a beaker containing 90 g. D.I. water (5 mol) and 30 g. Amberlyst 15 catalyst. The mixture was stirred at room temperature for 24 hrs. The conversion was >99%, and the yield was >95%.

Example 2

Synthesis of 4-vinylcyclohexene-1,2-diol (VCHD) from 4-vinylcyclohexene

2-A. Synthesis of a Mixture of 4-vinylcyclohexane-1,2-diformate, 4-vinylcyclohexane-1-hydroxy-2-formate, and 4-vinylcyclohexane-2-hydroxy-1-formate A one-liter 3-necked round flask was equipped with a mechanical stirrer, one dropping funnel, and a thermometer. 444 mL (13 mol) 96% formic acid and 130 mL (1 mole) 4-vinylcyclohexene (VCH) were charged to the flask. Under stirring, 106.9 g. (1.1 mol) 35% hydrogen peroxide solution was added dropwise at a rate of 1.5 mL per minute. After the addition was complete, the reaction mixture was stirred for two hours at 25–30° C. When the reaction was completed, the mixture became one clear phase. Water and formic acid were removed by vacuum distillation at 40–45° C. The residue oil was distilled under high vacuum in the presence of 2% cuprous chloride. The mixture of 4-vinylcyclohexane-1, 2-diformate, 4-vinylcyclohexane-1-hydroxy-2-formate, and a small amount of 4-vinylcyclohexane-1,2-diol were collected at 100–118° C. at 0.1 mm Hg. The yield was 71–80%.

2-B. Synthesis of a Mixture of 4-vinylcyclohexane-1,2-diformate, 4-vinylcyclohexane-1-hydroxy-2-formate, and 4-vinylcyclohexane-2-hydroxy-1-formate To a 30-gallon reactor equipped with a mechanical stirrer, and thermal couple, 10.82 Kg. 4-vinylcyclohexene (VCH) (100 mol) and 59.84 kg formic acid were charged and stirred at 100 rpm. 10.19 kg of 35% hydrogen peroxide was pumped into the reactor at about 150 mL/min. The mixture temperature was maintained at 25–30° C. After the addition of hydrogen peroxide was completed, the mixture was stirred for 5 hours. A small amount of sodium sulfite solution was added to test if there was hydrogen peroxide residue. The solution was distilled under vacuum to remove water and formic acid. The crude product mixture was obtained.

2-C. Hydrolysis of 4-vinylcyclohexane-1,2-diformate and 4-vinylcyclohexane-1-hydroxy-2-formate, and 4-vinylcyclohexane-2-hydroxy-1-formate The mixture obtained from Example 2-A was added in a 1 liter three-necked flask equipped with a mechanical stirrer, a dropping funnel, and a thermometer. 192 g (1.2 mol) 25% sodium hydroxide solution was added dropwise at 20–25° C. The mixture was stirred for 30 min. after the addition of sodium hydroxide solution. The mixture was allowed to stand for 2 hrs. for phase separation. The bottom aqueous solution of sodium formate was discharged, the crude VCHD diol was used as the starting material in the next step sulfonation reaction.

2-D. Hydrolysis of 4-vinylcyclohexane-1,2-diformate and, 4-vinylcyclohexane-1-hydroxy-2-formate, and 4-vinylcyclohexane-2-hydroxy-1-formate in 30 Gallon Reactor The crude product obtained in Example 2-B was stirred in the 30-gallon reactor at 20° C. 36.82 Kg. 25% sodium hydroxide solution was pumped in at a rate of 0.25 Kg./min. The temperature was kept below 25° C. After the addition, the mixture was stirred for 30 min. When the pH was stabilized at 10 or higher, the agitation was stopped and the mixture was slowly separated into two phases. The bottom aqueous phase was discharged and the top crude VCHD diol was used as the starting material for sulfonation reaction.

Example 3

Sulfonation of 4-vinylcyclohexane-1,2-diol (VCHD)

3-A. Sulfonation of 4-vinylcyclohexane-1.2-diol (VCHD) Prepared from Example 1-B to 4-(2-sulfoethyl) cyclohexane-1,2-diol, Sodium Salt (SECD)

37.545 grams (0.3585 mol) of $NaHSO_3$ and 6.787 grams of $Na_3PO_4.12H_2O$ (0.01785 mol) were dissolved in 64.3 grams of DI water as solution I. 0.3677 grams (0.00357 mol) of 35% $H_2O_2$ solution were dissolved in 50 grams of water as solution II. 50.79 grams (0.3572 mol) of 4-vinlycyclohexane-1,2-diol (VCHD) in a total 249 grams of aqueous solution was poured into a 1 liter 4-neck round bottom flask equipped with a mechanical stirrer, two addition funnels, thermometer, and a pH probe. Solution I was added at a rate of 2 ml/min. and solution II was added 1 ml/min. at 20–25° C. The solution was stirred at 300 rpm. During the reaction, the solution pH was in the range of 6–6.8. After the addition, the solution was stirred for 2 hrs.

3-B. Sulfonation of 4-vinylcyclohexane-1,2-diol (VCHD) to 4-(2-sulfoethyl) cyclohexane-1.2-diol, Sodium Salt (SECD).

37.545 grams (0.3607 mol) of $NaHSO_3$ and 6.787 grams of $Na_3PO_4 \cdot 12H_2O$ (0.01785 mol) were dissolved in 64.3 grams of DI water as solution I. 0.3677 grams (0.00357 mol) of 35% $H_2O_2$ solution were dissolved in 60 grams of water as solution II. 50.79 grams (0.3572 mol) of 4-vinlycyclohexane-1,2-diol (VCHD) in 192 grams of DI water was poured into a 1 liter 5-neck round bottom flask equipped with a mechanical stirrer, two addition funnels, thermometer, and a pH probe. Solution I was added at a rate of 2 ml/min. and solution II was added 1 ml/min. at 20–25° C. The solution was stirred at 300 rpm. During the reaction, the solution pH was in the range of 6–6.8. After the addition, the solution was stirred for 2 hrs.

Example 4

Oxidation of SECD to 3-(2-sulfoethyl) Hexanedioic Acid, Sodium Salt

4-A. Oxidation of SECD Prepared by Example 3A to 3-(2-sulfoethyl) hexanedioic acid, sodium salt (SEHA). The above solution was heated to 95° C. 0.89 grams (0.0035 mol) of tungstic acid was added into the solution and 110.3 grams (1.072 mol) of 35% hydrogen peroxide was added dropwise while stirring. The solution temperature was maintained at 97–100° C. for 8 hrs. and then followed with distillation to concentrate the solution to 62% of SEHA. After cooling down to room temperature, the final product was crystallized and filtered.

4-B. Oxidation of SECD to 3-(2-sulfoethyl) Hexanedioic Acid, Sodium Salt

The above solution was heated to 95° C. 0.89 grams (0.0035 mol) of tungstic acid was added into the solution and 110.3 grams (1.072 mol) of 35% hydrogen peroxide was added dropwise while stirring. The solution temperature was maintained at 97–100° C. for 3 hrs. and then followed with distillation to concentrate the solution to 62% of SEHA. After cooling down to room temperature, the final product was crystallized and filtered. The crude product was recrystallized to reach polymerization grade.

What is claimed is:

1. A process for making 4-(2-sulfoethyl) cyclohexane-1,2 diol sodium salt, said process comprising:

contacting 4-vinylcyclohexane-1,2-diol with a sulfonating agent in the presence of a buffer solution and an initiator, at ambient conditions, wherein the sulfonating agent is selected from the group consisting of sodium bisulfate and ammonium bisulfate and wherein the buffer solution is selected from the group consisting of alkali metal and ammonium phosphate, bicarbonates, and acetates.

2. The process of claim 1 wherein the sulfonating agent comprises sodium bisulfate.

3. The process of claim 1, wherein the buffer solution is selected from the group consisting of potassium phosphate, potassium acetate, ammonium phosphate, ammonium bicarbonate, ammonium acetate, sodium phosphate, sodium bicarbonate and sodium acetate.

4. The process of claim 1, wherein the initiator is selected from the group consisting of hydrogen peroxide, sodium persulfate and potassium persulfate.

5. The process of claim 1, wherein the 4-vinylcyclohexane-1,2-diol is prepared by a process comprising:

contacting 4-vinylcyclohexane-1,2-epoxide with water in the presence of a solid acidic catalyst at ambient conditions for a time sufficient to produce 4-vinylcyclohexane-1,2-diol.

6. The process of claim 1, wherein 4-vinylcyclohexane-1,2-diol is prepared by a process comprising:

contacting 4-vinylcyclohexane with formic acid in the presence of hydrogen peroxide to form a mixture A comprising at least one of 4-vinylcyclohexane 1,2-diformate, 4-vinylcyclohexane 1-formate 2-ol, 4-vinylcyclohexane 1-ol 2-formate, and 4-vinylcyclohexane-1,2-diol;

contacting mixture A with sodium hydroxide to accomplish hydrolysis of at least a portion of the compounds in mixture A to produce a mixture B comprising an aqueous phase and an organic phase; and separating the aqueous phase from the organic phase in mixture B, and obtaining an organic phase comprising essentially of 4-vinylcyclohexane 1,2-diol.

7. A process for making 3-(2-sulfoethyl) hexanedioic acid, sodium salt comprising: oxidizing 4-(2-sulfoethylcyclohexane)-1,2 diol sodium salt made by the process of claim 1 with hydrogen peroxide in the presence of tungstic acid.

8. The process of claim 1, wherein the buffer solution comprises ammonium phosphate.

9. The process of claim 1, wherein the buffer solution comprises sodium phosphate.

* * * * *